(12) United States Patent
Saalasti et al.

(10) Patent No.: US 10,856,794 B2
(45) Date of Patent: *Dec. 8, 2020

(54) METHOD AND SYSTEM FOR DETERMINING THE FITNESS INDEX OF A PERSON

(71) Applicant: Firstbeat Analytics Oy, Jyväskylä (FI)

(72) Inventors: Sami Saalasti, Jyväskylä (FI); Aki Pulkkinen, Jyväskylä (FI)

(73) Assignee: Firstbeat Analytics, Oy

( * ) Notice: Subject to any disclaimer, the term of this patent is extended or adjusted under 35 U.S.C. 154(b) by 201 days.

This patent is subject to a terminal disclaimer.

(21) Appl. No.: 16/152,818

(22) Filed: Oct. 5, 2018

(65) Prior Publication Data

US 2019/0029586 A1    Jan. 31, 2019

Related U.S. Application Data

(63) Continuation of application No. 14/110,172, filed as application No. PCT/FI2012/050359 on Apr. 12, 2012, now Pat. No. 10,123,730.

(30) Foreign Application Priority Data

Apr. 12, 2011 (FI) .................................... 20115351

(51) Int. Cl.
*A61B 5/22* (2006.01)
*A61B 5/0205* (2006.01)
(Continued)

(52) U.S. Cl.
CPC .............. *A61B 5/222* (2013.01); *A61B 5/024* (2013.01); *A61B 5/0205* (2013.01); *A61B 5/221* (2013.01);
(Continued)

(58) Field of Classification Search
CPC ............ A61B 5/22; A63B 24/00; G06F 19/00
See application file for complete search history.

(56) References Cited

U.S. PATENT DOCUMENTS 6,529,771 B1  3/2003 Kieval et al.
6,882,955 B1  4/2005 Ohlenbusch et al.
(Continued)

FOREIGN PATENT DOCUMENTS

WO  2007/099206 A1  9/2007
WO  2008/003830 A1  1/2008
(Continued)

OTHER PUBLICATIONS

European Search Report dated Aug. 21, 2014, in corresponding European patent application No. 12771009.3 (2 pgs.).
(Continued)

*Primary Examiner* — Alyssa M Alter
(74) *Attorney, Agent, or Firm* — Samuel M. Korte; Max M. Ali

(57) ABSTRACT

The invention relates to a method and system for determining the cardiorespiratory fitness level of a person, with the aid of freely performed exercise, in which training: the physiological intensity of the person is measured periodically during the exercise session, the external work output of the exercise session is measured simultaneously relative to the measured intensity, from each period's measured intensity value and external work output, the representativeness of the values measured is determined, in order to determine the fitness level using the following criteria: the physiological intensity should be stabilized relative to the external work output, the external work output should be within a selected range, the physiological intensity should be greater than a selected lower limit, in which case, a fitness level
(Continued)

estimate is defined for each accepted period as well as a fitness from several estimates.

15 Claims, 8 Drawing Sheets

(51) Int. Cl.
*A61B 5/024* (2006.01)
*A61B 5/00* (2006.01)
*G06F 19/00* (2018.01)
*G16H 50/30* (2018.01)
*G16H 20/40* (2018.01)
*G16H 20/60* (2018.01)
*A61B 5/08* (2006.01)
*A61B 5/083* (2006.01)

(52) U.S. Cl.
CPC .......... *A61B 5/4866* (2013.01); *A61B 5/4884* (2013.01); *A61B 5/7264* (2013.01); *G06F 19/00* (2013.01); *G06F 19/3481* (2013.01); *G16H 20/40* (2018.01); *G16H 20/60* (2018.01); *G16H 50/30* (2018.01); *A61B 5/0816* (2013.01); *A61B 5/0833* (2013.01); *A61B 5/741* (2013.01)

(56) References Cited

U.S. PATENT DOCUMENTS

| | | | |
|---|---|---|---|
| 10,123,730 B2* | 11/2018 | Saalasti | ............... A61B 5/0205 |
| 2002/0039952 A1 | 4/2002 | Clem | |
| 2007/0232455 A1 | 10/2007 | Hanoun | |
| 2011/0040193 A1 | 2/2011 | Seppanen et al. | |
| 2012/0029370 A1 | 2/2012 | Rocker et al. | |

FOREIGN PATENT DOCUMENTS

| | | |
|---|---|---|
| WO | 2009/133248 A1 | 11/2009 |
| WO | 2010/112010 A1 | 10/2010 |

OTHER PUBLICATIONS

International Preliminary Report on Patentability dated Aug. 13, 2013, in corresponding PCT Application No. PCT/FI2012/050359 (11 pgs.).

International Search Report dated Aug. 23, 2012, in corresponding PCT Application No. PCT/FI2012/050359 (3 pgs.).

* cited by examiner

METHOD AND SYSTEM FOR DETERMINING THE FITNESS INDEX OF A PERSON

CROSS-REFERENCE TO RELATED APPLICATIONS

This application is a continuation of U.S. patent application Ser. No. 14/110,172, filed Oct. 7, 2013, which is a national stage application of International Application No. PCT/FI2012/050359, filed Apr. 12, 2012, which claims priority to Finnish Patent Application No. 20115351, filed Apr. 12, 2011, the entire contents of which are incorporated herein by reference.

BACKGROUND TO THE INVENTION

1. Scope of the Invention

The present invention relates to a method and system for determining the cardiorespiratory fitness level of a person, with the aid of freely performed exercise, in which exercise
 the physiological intensity of the person is measured periodically during the exercise session
 the measured intensity is measured simultaneously with the external work output of the exercise session.
 In the system, there is
 an interface device containing input devices for entering optional user-specific initial parameters prior to the exercise and a feedback means for giving feedback,
 a memory register for recording the values of the said parameters and computation variables,
 first means for measuring and recording a variable proportional to the physiological intensity,
 second means for registering and recording the external work output simultaneously relative to the measurement of the physiological intensity.

2. Description of the Prior Art

Most wristop devices equipped with a heart rate monitor guide exercise in a selected manner. The user selects an operating mode, which can be, for example, the achievement of a selected training effect, an increase in endurance, or a reduction in weight. User-specific parameters, which are, for example, sex, age, weight, and height, are entered in the device when it is begun to be used. It is easy for the user to set these data in the device. However, it is difficult for the user to provide, for example, information on the maximum heart rate level (HRmax) and the fitness level (VO$_2$max), as well as the activity class. As such, it is already known that a device (for example, a heart rate monitor) can propose, for example, increasing the HRmax value, if a heart rate value higher than the default value or set value appears in use.

Nowadays, web-based services are also popular, in which the data of the heart rate monitor are transmitted through the internet to a server, with the aid of which a computer program, performing physiological computation, is used. Publication US 2007/0082789 A1 discloses a method for m determining a person's performance from physical exercise. The method cannot, however, be utilized during exercise, but instead requires the data to be analysed separately after exercise.

A method is known from publication WO 2009/133248 for determining a free fitness level from exercise, in which heart rate and external output, such as, for example, speed and height together, are measured periodically. A bicycles ergometer and many other exercise devices give the external output directly and, if the speed of running exercise, for example, is measured together with altitude information, it is possible to determine what the external work output is. With the aid of free exercise, as long as there is enough data, the level of the fitness of the user's respiratory and cardio-vascular system (cardiorespiratory) fitness level can be determined. However, the method requires relatively long (30 s-4 min) stable periods. The method is difficult to apply to the automatic determining of fitness level.

Publication US 2012/0029370 (WO 2010/112010 A1) discloses a method using short standard loadings to determine fitness level.

The present invention is intended to avoid the drawbacks of the known methods and systems relating to their difficult start-up considering the initial data required or precisely controlled exercise. The characteristic features of the method according to the invention are stated in the accompanying claim 1 and the features of the system implementing the method are stated in claim 3. The method according to the invention can effectively utilize short periods of, for example, five seconds, which are defined as representative, in terms of the determining of the fitness level, using selected criteria relating to the simultaneous physical-intensity and external work values.

To be able to evaluate fitness on the basis of heart rate, it is important to be able to exclude certain loading stages, which do not produce a reliable result. For example, particularly during recovery, the physiological intensity (e.g., heart rate) is considerably higher when compared to external work output (e.g., running speed). If fitness were to be estimated from these recovery periods too, the real fitness level would be considerably underestimated.

The loading stage can be evaluated, for instance, on the basis solely of the behaviour of the heart rate (heart rate increases, decreases, or remains constant), or together with external work-output (heart rate increases, decreases, or remains constant simultaneously with the external work output, or in a specific relation to it). The loading stage can also be evaluated, for example, with the aid of a variable (such as EPOC) depicting a change in m the homeostasis (at least an increasing variable will eliminate a recovery from the loading stages).

With the aid of the method according to the invention, a wristop device can be easily made to create the user's fitness level and to update it during use.

If at least the so-called difficult initial parameters, i.e. the parameters depicting the user's internal data, particularly their fitness level, are each taken initially into the calculation as a preselected default value, the system can update their value gradually to the physiologically correct value.

In a preferred embodiment, the user is asked by software means contained in the system or device for external parameters such as sex, age, weight, and height. The fitness level, e.g., the VO$_2$max, and the maximum heart rate HRmax are taken initially as default values. The HRmax value always begins immediately to slide to the right towards the physiological maximum value when the user exceeds the highest previous maximum heart rate level measured under stress. The updating of the fitness index, on the other hand, demands data, i.e. that the user performs one or even several exercise sessions, which produce periods accepted when determining the fitness index.

In a preferred embodiment, automatic calculation of the fitness index takes place in a simpler manner than that presented in the WO publication. A model is created from empirical material to depict the VO$_2$max, for example, ml/kg/min, i.e. oxygen consumption per minute per kilogram of weight, using intensity as the variable, in a preferred form from the relative heart rate (% HRmax) and external work output. Next, each heart rate signal datum recorded from the user's free exercise is processed and suitable periods are sought from it, for example, using the following criteria:

stable loading state
external work output in the selected range
heart rate above a set criterion (x % HRmax)

The accepted level should be in a stable loading stage, i.e. the heart rate should be stabilized relative to the external work output. This criterion is preferred met when the EPOC value is rising.

Each accepted period gives a VO$_2$max estimate (FI$_n$) from the said model. The final single VO$_2$max value of a single exercise session is obtained by calculating either the average, or the weighted average from the VO$_2$max estimates of the accepted periods.

Mathematical formulas are

Fitness index(average)=$\Sigma FI_n$

In one embodiment, the user's activity class is also an automatically updated value, so that its preselected default value gradually approaches the correct value. It preferably determined from a 3-dimensional table, or a function depicting it, in which the axes of the table are activity class, age, and sex.

In summary, it can be stated that the invention permits the fitness level to be determined from the user's arbitrary exercise performance, provided there are sufficiently intensive portions in it. When applying the invention in a wristop device or similar, the two main benefits of the invention are, firstly, the easier start-up of the device or product and, secondly, the automatic increase in precision and calibration to the fitness level through use. If previously it has been desired to exploit information on the fitness level in feedback or guidance, the fitness level has had to be estimated indirectly, making the feedback given or the functionality imprecise. The fitness level can also be measured precisely, for example, using laboratory tests, and after this entered manually into the device, but this is not very practical and demands considerable effort and arrangements from the user, so that it is seldom practical.

The fitness level varies and/or changes continuously due to the effect of several different factors, such as, for example, stress and tiredness, as well as the recovery state, illnesses, or aging. Thus, if the user's fitness level is calibrated automatically, it will ensure the accuracy, correctness, and suitability to the user in different situations, of the feedback given to the user. If no allowance is made for changes taking place in the fitness level, or if wrong estimates of the fitness level are used, the feedback can be erroneous and, in the worst case even detrimental to the user.

Central Concepts
User-Specific Initial Parameter:

Information depicting the person, which can be, for example, age, height, weight, sex, maximum heart rate (HRmax), fitness level, i.e. maximum oxygen consumption (VO$_2$max), activity class, or some other personal information.

External Work Output:

External work output is a person's external measured work output achieved when moving, such as, for example, a person's running speed, or running speed on a specific piece of ground, rising or falling angle of a treadmill, or measured using an output measuring device in free performance, or some other movement, for example, using an acceleration sensor, or output measured in some other way. External work output can also be calculated from a person's specific known performance, for example from the running time over a known distance, based on the length of stride when running, step contact, or step density. External work output can be converted, for example, converted into oxygen consumption (VO$_2$) or energy consumption, in which case it will depict the amount of oxygen or energy consumed when a person moves at the output in question. Thus, external work output can be measured or estimated, for example, as continuous data during exercise, or as a single average depicting the entire exercise session.

Fitness Level:

A person's aerobic, i.e. endurance condition, the (cardiorespiratory) condition level, or performance capacity of the respiratory and cardiovascular system. Fitness level can be depicted using parameters (fitness index), which can be, for example, maximum oxygen intake (VO$_2$max), METs (=VO$_2$max/3.5), maximum work output defined in watts, for example from a bicycle ergometer test, or using an output measuring device in free exercise, maximum running speed in a maximum running test, or in free running taking into account altitude data, a Cooper test result, the fastest time for running a specific distance (e.g., 3, 5, or 10 km), or some other external measured endurance performance depicting maximum work output. The fitness level can be measured or estimated, for example, using various direct or indirect fitness tests, for example, using a free fitness test like that described, various evaluation methods, for example Jackson et al. 1990, using various questions (e.g., "are you able to run 3 km non-stop?", "are you able to walk with a reasonably strenuous output non-stop for 10 minutes?", or in a similar manner), on the basis of the answers to which the fitness level can be estimated, or else using the person's own subjective evaluation.

Physiological Intensity of Exercise:

This tells the output at which the person moves. The physiological intensity of exercise depicts, for example, the heartbeat frequency of the person's heart, i.e. their heart rate. The intensity can be scaled relative to the person's fitness level, i.e. their maximum performance, so that it tells at what output the person moves relative to their own maximum. The heart rate can be scaled at the person's maximum heart rate and a percent intensity of the maximum heart rate (HRmax) can m be obtained. Other variables depicting physiological intensity can be, for example, the person's frequency of respiration, their oxygen consumption (VO$_2$), or their ventilation. The intensity of exercise can also be the external measured work output, or activity, measured, for example, using an acceleration sensor in a preferred form relative to the person's maximum external work output. Intensity can also be estimated on the basis of the person's subjective feeling. Thus, the physiological intensity can be measured or estimated, for example, as continuous data during exercise.

The Loading Stage of Exercise:

In exercise performance, there are several different loading stages, during which the body's physiological state and functions, i.e. the physiological intensity, are regulated to correspond in the best possible manner to correspond to the external work output. The loading stages are, for example, the on response, i.e. the body's response to the start of exercise; the steady state, i.e. the stabilized physiological intensity when the external work output is constant; and the off response, i.e. recovery, when the external work output decreases or stops altogether. In freely performed exercise, the various loading stages alternate naturally with each other, partly merging according to, among other things, the shapes of the ground (uphill, downhill) and the performance of the exercise (breaks for instance for traffic lights, etc.). In terms of evaluating fitness on the basis of heart rate, it is important to exclude certain loading stages that do not produce a reliable result. For example, especially during recovery the physiological intensity (e.g., heart rate) is considerably higher relative to the external work output (e.g., running speed). If fitness were to be evaluated also during their recovery periods, the real fitness level would be considerably underestimated. A loading stage can be evaluated, for instance, on the basis of heart rate behaviour (the heart rate rises, falls, or remains constant) solely, or in combination with the external work output (the heart rate rises, falls, or remains constant simultaneously with the external work output, or in a specific relation to it). A loading stage can also be evaluated, for example, with the aid of a variable (such as EPOC) depicting a change in homeostasis (a variable that is at least increasing will exclude the recovery loading stage).

DETAILED DESCRIPTION OF THE INVENTION

Figure 1:
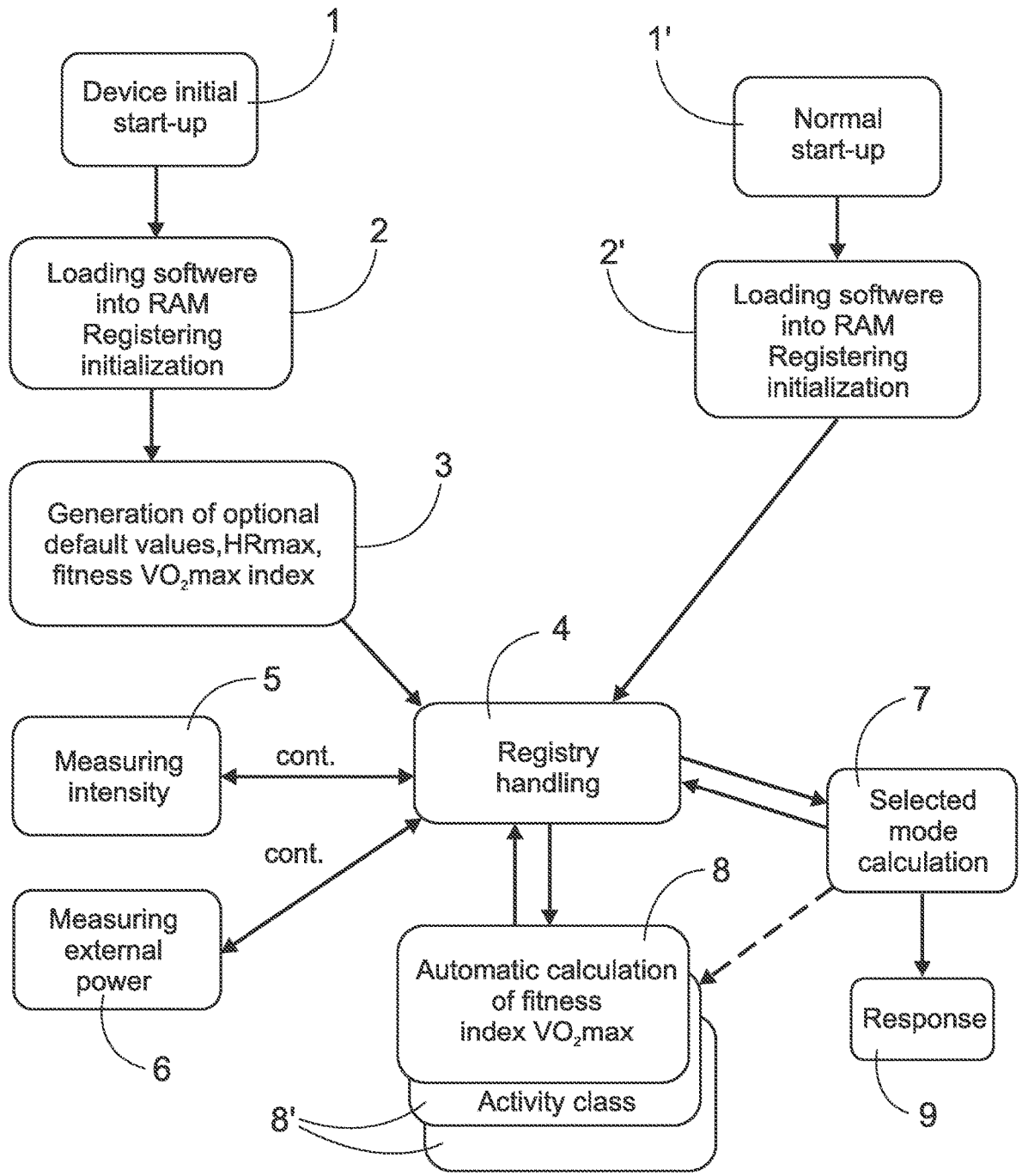
FIG. 1 shows a flow diagram of a system monitoring a user's physical state.

According to FIG. 1, in the system according to the invention, additional attention is paid to the start-up 1, compared to the start-up 1' of conventional use. After the loading 2 of the program and the initiation of the registers, during the first operating session the optional default values are generated, point 3. Later, loading 2' the program leads directly to processing 4 of the computation registers, in which at the same time measurement 5 of intensity and measurement 6 of external work output are initiated, for example (position and altitude data obtained from a GPS service). The computation registers contain continuous real-time information on the user's intensity and external work output. The user's intensity is usually the measured heart rate value. The external work output can be obtained in many ways, depending on the kind of the exercise and the devices used. A GPS device used in connection with wristop devices provides altitude data, which is one alternative. The altitude data is optional and is not necessary if the exercise session takes place on level ground. The exercise device, such as, for example, a bicycle ergometer, can provide the external work output directly.

In a preferred embodiment, after initiation of the program has been commenced, on the first time it asks the user for external data, such as sex, age, weight, and height. Alternatively, these too are default values, which the user corrects if they wish.

Conventionally, the device has some selected operating mode 7, i.e. manner of use, which aims at some desired end result, for example a selected level of energy consumption, and provides feedback 9 on it.

Because particularly the fitness level is required in the calculation of many of the target variables, it is calculated automatically with the aid of calculation devices 8 belonging to the system. Other data, such as maximum heart rate HRmax and the activity class, are preferably updated in the same way.

Figure 2:
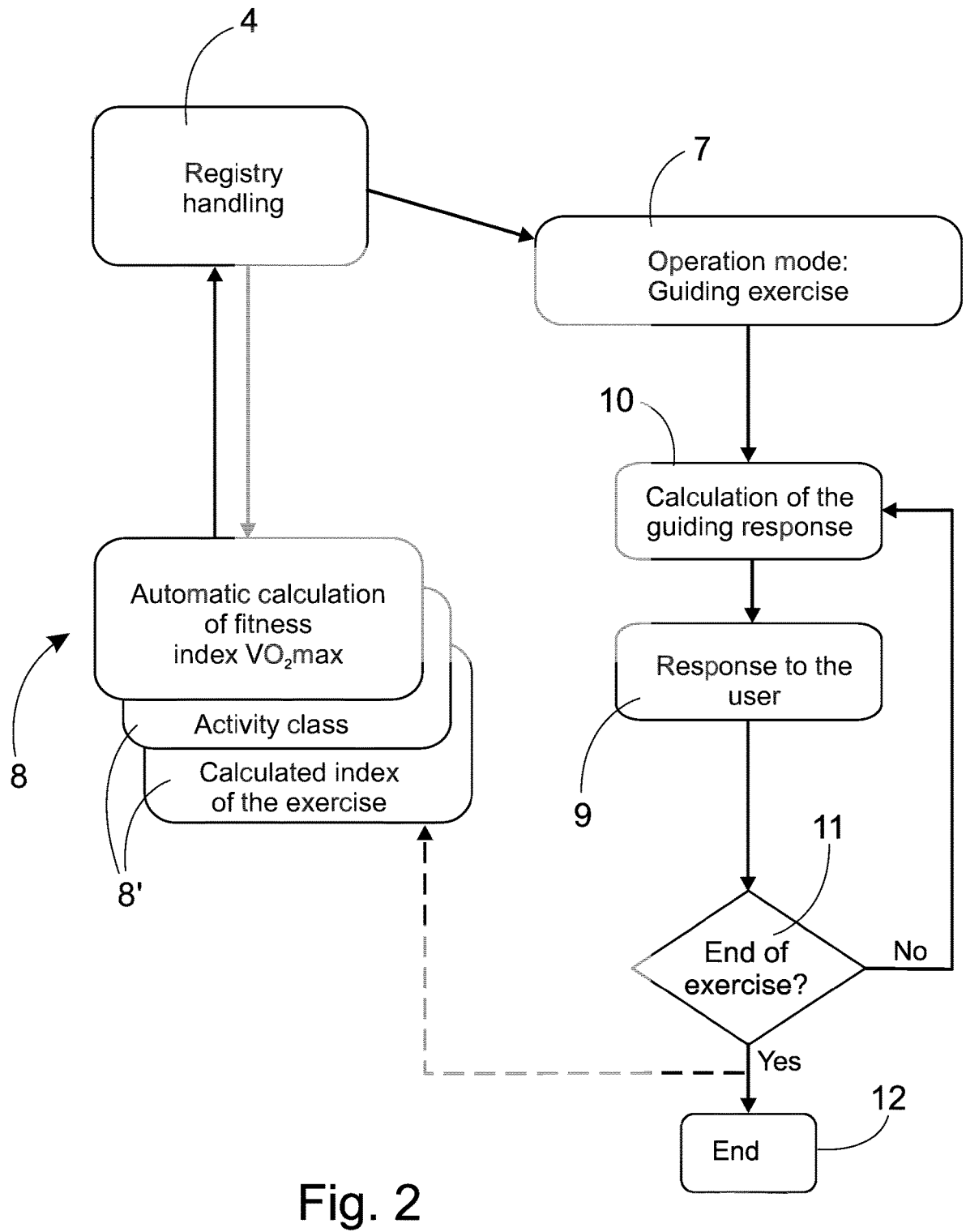
FIG. 2 shows the system of FIG. 1 applied to guiding training.

In FIG. 2, the usual operating mode 7 of FIG. 1 is exercise guidance. The target of the exercise can be, for example, achieving a selected training effect, or exercise for reducing weight. In order to achieve the target, the user is provided with continuous feedback, i.e. whether the intensity is suitable or too high/low for achieving the target within the set time. The guidance feedback is calculated on the basis of the register data at point 10. The provision of the guidance feedback 11 is checked by a conditional statement 11, if the exercise has been completed. If the exercise is still under way, a return is made to the calculation of the guidance feedback, otherwise exit to the end 12 of the routine. In FIG. 2, it should be noted that the automatic update routine (8, 8') can also obtain a parameter value from the exercise, which is automatically updated in the computation register. This can be, for example, the value of the fitness index, which is calculated only after the exercise and not continuously.

Figure 3:
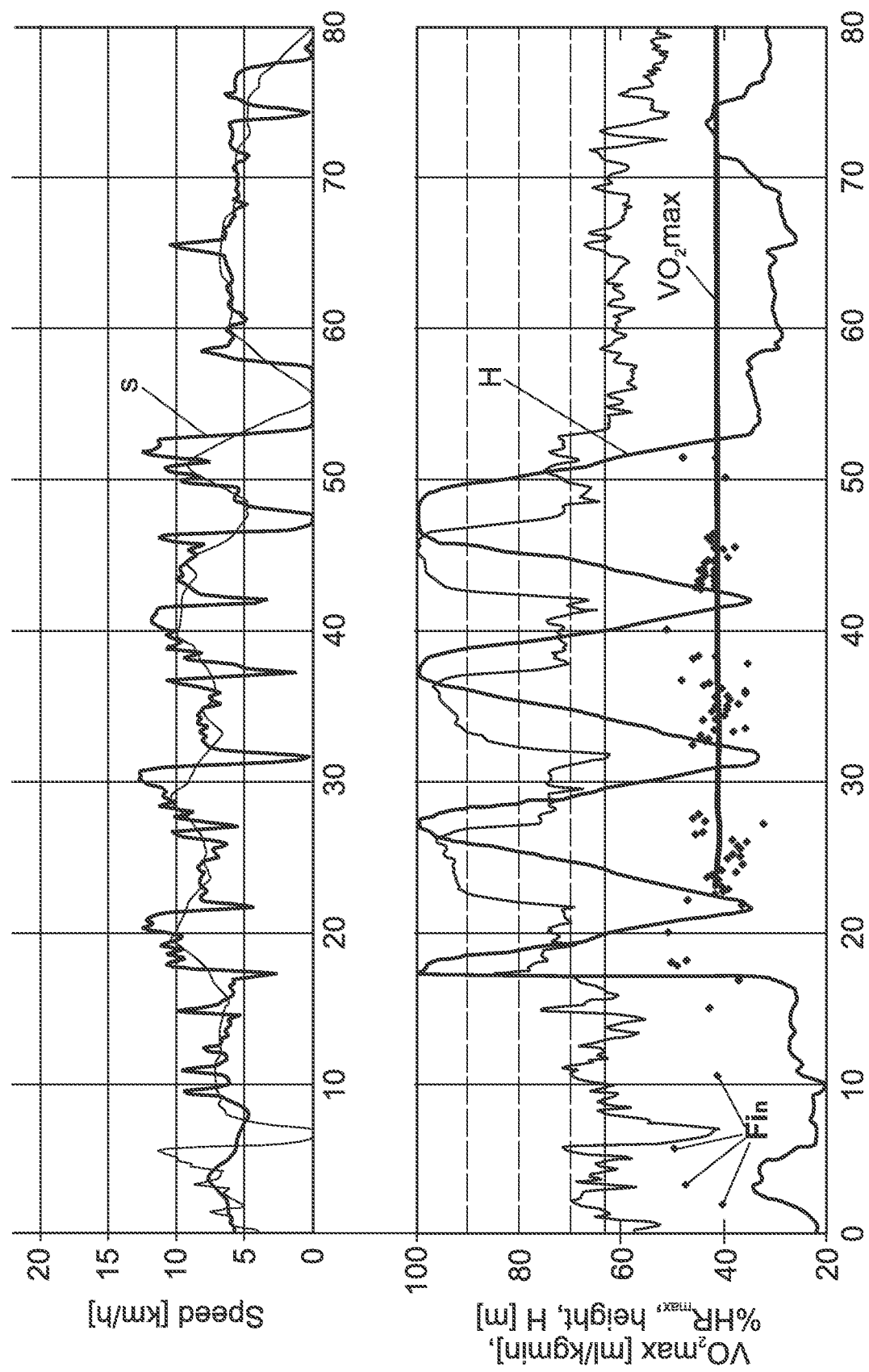
FIG. 3 shows graphically the determining of the fitness level.

FIG. 3 illustrates the calculation of the fitness level value by means of a preferred method. The graph in the upper part of the figure shows the momentary speed (km/h) in running exercise and its mean value as the exercise proceeds. In the lower part of the figure, the relative heart rate value % HRmax (0-100% of the maximum heart rate value), the altitude in metres, and the computed fitness level estimates $(FI_n)$ ($VO_2$max ml/kg/min), calculated in five-second intervals, are shown on the same time scale. At about four minutes, the acceptable data are sufficient and there is a thick line in the graph showing the fitness level computed from the points e obtained. Each value of the fitness level $(FI_n)$ is obtained from the modelled function f(W, Int) by entering into it the relative heart rate (Int) and external work (W) of the accepted segment. The modelled function f(W, Int) is obtained with the aid of numerous test exercise sessions performed by test persons. The exercise sessions of the selected group were monitored for a period of several months and at regular intervals their fitness level was measured using a clinical method. From the data obtained and previously known information on the relation between the external work output and oxygen consumption, a modelled function depicting fitness level was formed, with heart rate and external work as the variables. The data collected also included sex, age, and weight, by means of which the modelled function can be focussed more precisely on each user.

The calculation of the fitness level estimate from simultaneous physiological-intensity and external-work values is computed, in one embodiment, as follows. It is generally known, that, by comparing the HRmax heart rate the theoretical work output and in turn by extrapolating the maximum heart rate, a rough estimate of m the fitness level can be obtained.

In the literature, a basic equation is known for running exercise:

$$VO_2max\ (ml/kg/min) = 11.1 * speed\_ms + 5.3333$$

Here, the following equation is derived from it, which takes slope into account:

$$VO_2max = (-c1 * hr/maximal\_hr + (1+c1)) * (11.1 * (c2 * angled + 1) * speed\_ms + 5.3333)$$

$VO_2max$ ml/kg/min, the momentary $VO_2max$ value i.e. estimate hr BPM instantaneous, momentary heart rate level maximum hr BPM, the person's background parameter (maximum heart rate level)
angles in radians, momentary running angle
speed_ms m/s, momentary running speed
$c1$, $c2$, parameters optimized from empirical material A corresponding equation is created for each form of external work output, in such a way that the calculated $VO_2max$ corresponds to the real value.

Figure 4:
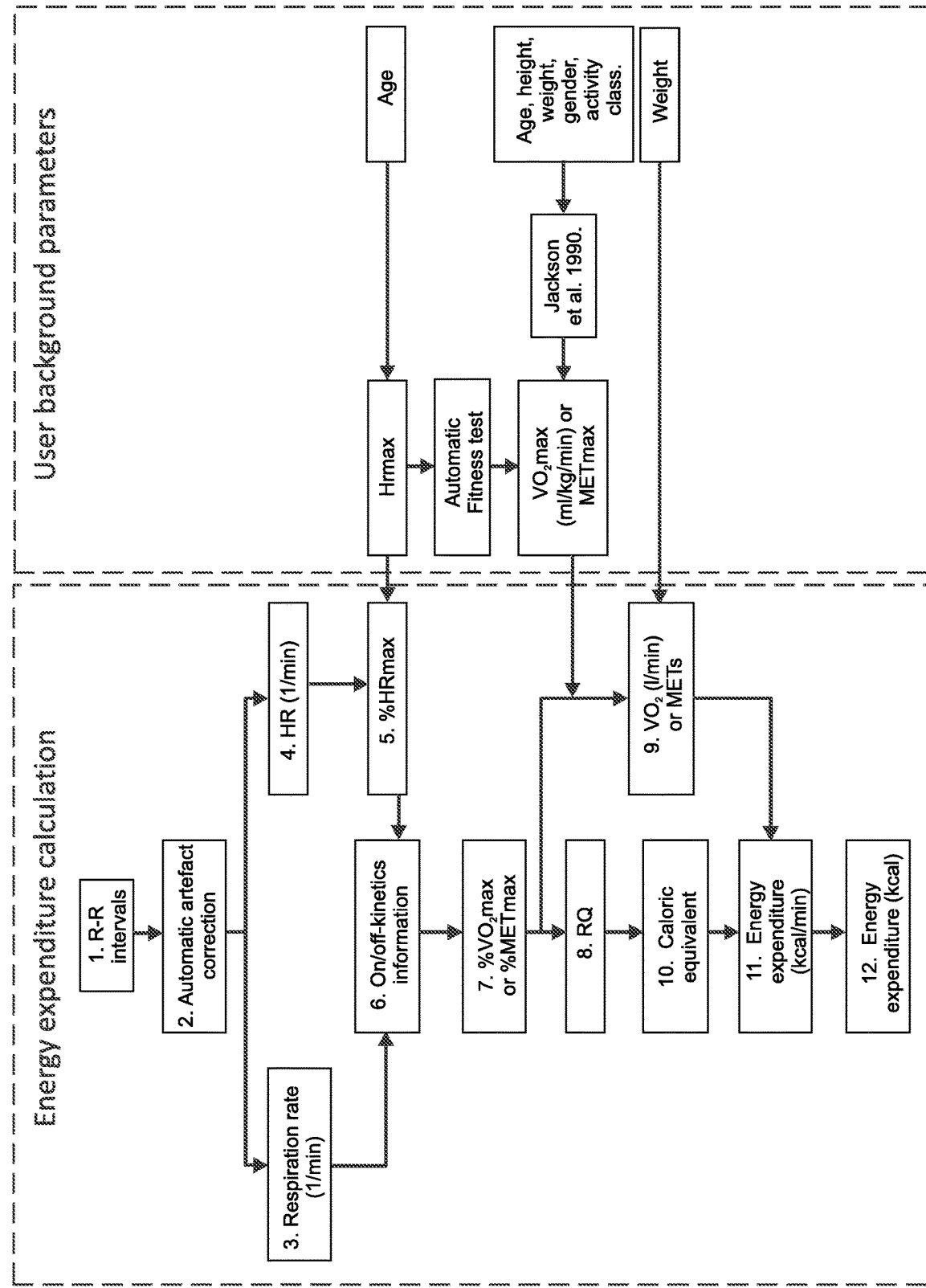
FIG. 4 shows a flow diagram in the calculation of energy consumption.

Example of Application 1 (FIG. 4). Calculation of Energy Consumption

Automatic determining of the fitness level can be used, for example, in the calculation of energy consumption. The calculation of energy consumption generally requires the person's age, height, weight, sex, and the activity class that depicts the level of the person's physical activity. On the basis of these data, it is possible to estimate, using, for example, the equation developed by Jackson et al. (1990), the person's fitness level, i.e. the maximum oxygen consumption ($VO_2max$ or METmax), which can be used in calculating the energy consumption, see FIG. 4.

In an automatic system, a person can only be asked, for example, their age, sex, and weight, so that the rest of the person's background data are set as certain default values, on the basis of which calculation of $VO_2max$ takes place using the aforementioned Jackson equation. On the basis of age, it is possible to use the traditional equation to calculate the maximum heart rate 210−(age*0.65)=maximum heart rate HRmax, which is the necessary variable for performing a fitness test. After this, $VO_2max$ is computed from exercise performed by the person, which gives a more precise value for the original estimate of $VO_2max$. This more precise estimate of $VO_2max$ is then used in the calculation of the energy consumption.

Age and weight can also be preset, in which case the person will not need to enter any personal background data. The automatically calculated and updated $VO_2max$ keeps the system accurate.

Oxygen consumption can also be calculated in a corresponding manner to energy consumption.

FIG. 4 shows an example of the computation model for energy consumption, in which the $VO_2max$ value calculated automatically from exercise sessions reduces or entirely eliminates the entering of the personal background data set at the start. Thus the product is considerably easier to start up, and in addition the product always produces m accurate information on energy consumption, even though the person's fitness changes.

1. RR data, i.e. a time series of the time always between two consecutive heartbeats.
2. The heartbeat interval data is corrected by automatic error correction.
3. Respiratory frequency information is calculated from the heartbeat interval data.
4. The heart rate per minute is calculated from the heartbeat interval data.
5. The heart rate is converted to % of the person's maximum heart rate, using the person's maximum heart rate. The maximum heart rate is defined on the basis of the person's age, if the person does not know it directly.
6. The on/off kinematic information (loading stage) is calculated on the basis of the respiratory frequency and % HRmax.
7. % $VO_2max$ or METmax intensity is calculated, i.e. the physical loading exertion level as percentages relative to the person's maximum.
8. The RQ (respiratory quotient) value is calculated, which gives the ratio of fats and carbohydrates as energy sources.
   The RQ relates to a known way to calculate energy consumption on the basis of oxygen consumption. Generally, oxygen consumption (litre/minute) is multiplied by five, giving the energy consumption in calories.
9. The relative intensity % $VO_2max$ is converted to absolute oxygen consumption by multiplying it by the person's $VO_2max$ (maximum oxygen consumption). If the person does not know their $VO_2max$ value, it can be calculated using Jackson et al.'s 1990 equation, on the basis of the person's background data. The $VO_2max$ value can also be obtained on the basis of an automatic fitness test. All the person's background data can be set as default values, in which case the automatic fitness test will make the $VO_2max$ value more precise, as exercise sessions accumulate.
10. The calorific equivalent is calculated, which tells on the basis of the RQ value how much energy is produced per litre of oxygen consumed.
11. The momentary energy consumption kcal/min is calculated.
12. The sum of energy consumption kcal is calculated.

Figure 5:
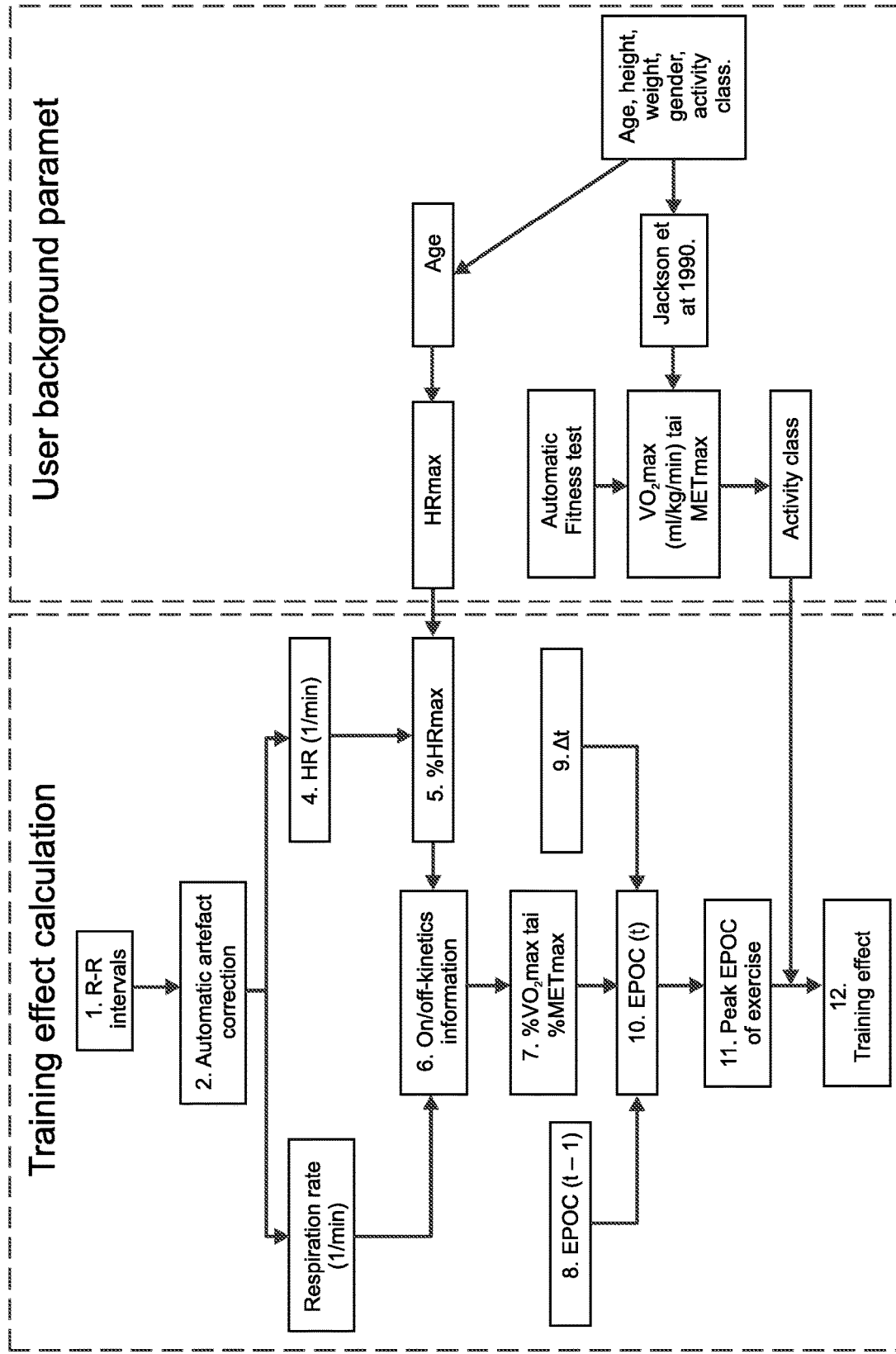
FIG. 5 shows a flow diagram in the calculation of training effect.

Example 2 of Application (FIG. 5). Calculation of Training Effect

The automatic determining of fitness level can be used, for example, in the calculation of the training effect. Typically, age and activity class from the person's background data are used in the calculation of the training effect, see FIGS. 5 and 6. The activity class can be determined on the basis of the result of a free fitness test, $VO_2max$, together with age and sex, so that the person need not known their activity class, see Table 1.

FIG. 5. Calculation of training effect.
1. RR data, i.e. a time series of the time always between two consecutive heartbeats.
2. The heartbeat interval data is corrected by automatic error correction.
3. Respiratory frequency information is calculated from the heartbeat interval data.
4. The heart rate per minute is calculated from the heartbeat interval data.
5. The heart rate is converted to % of the person's maximum heart rate, using the person's maximum heart rate. The maximum heart rate is defined on the basis of the person's age, if the person does not know it directly.
6. The on/off kinematic information (loading stage) is calculated on the basis of the respiratory frequency and % HRmax.
7. % $VO_2max$ or METmax intensity is calculated, i.e. the physical exertion level as percentages relative to the person's maximum.

8.-10. EPOC (Excess Post-exercise Oxygen Consumption) is calculated at the present moment t, using $VO_2$max intensity (7), as well as the previous EPOC value (8) and the duration (9) of the time interval being examined.

11. The exercise's EPOC peak, i.e. the highest EPOC value so far, is calculated.

12. The EPOCpeak value is converted to Training Effect by using the activity class according to FIG. 3. If the person does not know their activity class, it is set to a specific value as a default, or is calculated from the $VO_2$max value in the manner of Table 1, using either an automatic fitness test, or the $VO_2$max value estimated by Jackson et al. 1990. All of the person's background data can be set to be default values, in which case the automatic fitness test will make the $VO_2$max value more precise as training accumulates.

Figure 6:
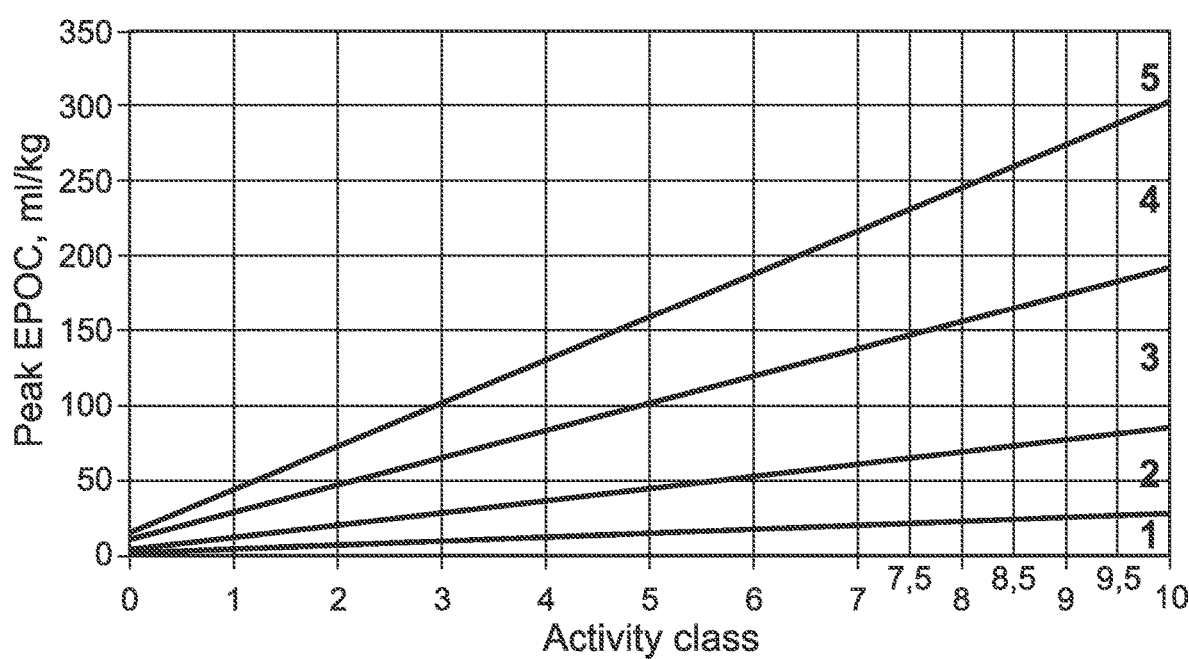
FIG. 6 shows a set of curves for determining training effect.

According to FIG. 6, the training effect can be determined on the basis of the training's highest EPOC value as well as the person activity class. The person's activity class can be determined automatically on the basis of the automatically updated fitness level ($VO_2$max). The following Table 1 shows the $VO_2$max values according to age and sex for determining the activity class. These two sub-tables together form a 3-dimensional table, in which the axes are age, sex, and activity class. In each cell contains a $VO_2$max value determined by these variables. The activity class is found by searching for the correct column with the aid of age and sex, from which the known $VO_2$max value is sought, on the row of which the activity class is sought.

TABLE 1

| | | Age | | | | |
|---|---|---|---|---|---|---|
| | | <29 | 30-39 | 40-49 | 50-59 | >60 |
| | | Men | | | | |
| Act. class | 0 | 34.5 | 32.5 | 30.9 | 28 | 23.1 |
| | 1 | 37.1 | 35.4 | 33 | 30.2 | 26.5 |
| | 2 | 39.5 | 37.4 | 35.1 | 32.2 | 28.7 |
| | 3 | 41 | 38.9 | 36.7 | 33.8 | 30.2 |
| | 4 | 42.5 | 41 | 38.1 | 35.2 | 31.8 |
| | 5 | 44.2 | 42.4 | 39.9 | 36.7 | 33.6 |
| | 6 | 46.8 | 44.6 | 41.8 | 38.5 | 35.3 |
| | 7 | 51.4 | 50.4 | 48.2 | 45.3 | 42.5 |
| | 7.5 | 61 | 61 | 61 | 61 | 61 |
| | 8 | 65 | 65 | 65 | 65 | 65 |
| | 8.5 | 69 | 69 | 69 | 69 | 69 |
| | 9 | 73 | 73 | 73 | 73 | 73 |
| | 9.5 | 77 | 77 | 77 | 77 | 77 |
| | 10 | 81 | 81 | 81 | 81 | 81 |
| | | Women | | | | |
| Act. Class | 0 | 28.4 | 26.5 | 25.1 | 22.3 | 20.8 |
| | 1 | 30.6 | 28.7 | 26.5 | 24.3 | 22.8 |
| | 2 | 32.3 | 30.5 | 28.3 | 25.5 | 23.8 |
| | 3 | 33.8 | 32.3 | 29.5 | 26.9 | 24.5 |
| | 4 | 35.2 | 33.8 | 30.9 | 28.2 | 25.8 |
| | 5 | 36.7 | 34.6 | 32.3 | 29.4 | 27.2 |
| | 6 | 38.1 | 36.7 | 33.8 | 30.9 | 29.4 |
| | 7 | 44.2 | 41 | 39.5 | 35.2 | 33 |
| | 7.5 | 55 | 55 | 55 | 55 | 55 |
| | 8 | 59 | 59 | 59 | 59 | 59 |
| | 8.5 | 63 | 63 | 63 | 63 | 63 |
| | 9 | 67 | 67 | 67 | 67 | 67 |
| | 9.5 | 71 | 71 | 71 | 71 | 71 |
| | 10 | 75 | 75 | 75 | 75 | 75 |

From Table 1, the person's activity class $VO_2$max can be determined on the basis of sex and age. The activity class can, in turn, be used, for example, to determine the training effect from the EPOC value.

Example 3 of Application. Selection of Training Programme

The automatically determined fitness level can be used in the selection or adjustment of the training programme. Typically, the person must estimate their activity class, or the activity class is determined on the basis of the person's activity history. On the basis of the result $VO_2$max of the fitness test determined on the basis of a free fitness test, the training programme can be selected directly to suit the person's fitness level, or the activity class can be calculated on the basis of Table 1 and the programme determined on its basis, see Table 2. Table 2 shows training programmes (table row). The desired training programme can be selected on the basis of the activity class calculated (Table 1) from $VO_2$max ("original activity class" in the table).

In a preferred solution, the $VO_2$max data obtained on the basis of an automatic fitness test from several training sessions by the same person is used. In the best case, the reliability of the estimation of the $VO_2$max of each individual training session, and how much reliable material has been found temporally from the training, can be used in the weighting. If the amount of reliable data is 5, 10, 15, 20, 25, 30, 40, or 50 minutes, the corresponding weighting coefficients as percentages are 10, 20, 30, 40, 50, 60, 80, and 100%, in that order. For example, if reliable material has been obtained from 4 minutes of the entire training in the automatic test, this new $VO_2$max value is added to the $VO_2$max average values of the previous test using a weighting coefficient of 8%, and correspondingly the amount of reliable material by 30 min with a weighting coefficient of 60%. Naturally, it is preferable for the $VO_2$max of the first training session to be calculated with a weighting coefficient of 100%, because it probable that this value will be more correct than the preselected $VO_2$max value, the $VO_2$max value calculated using the equation of Jackson et al. 1990 on the basis of the person's background data, or the $VO_2$max value calculated using the equation of Jackson et al. 1990 on the basis of the person's preselected background data.

Figure 7:
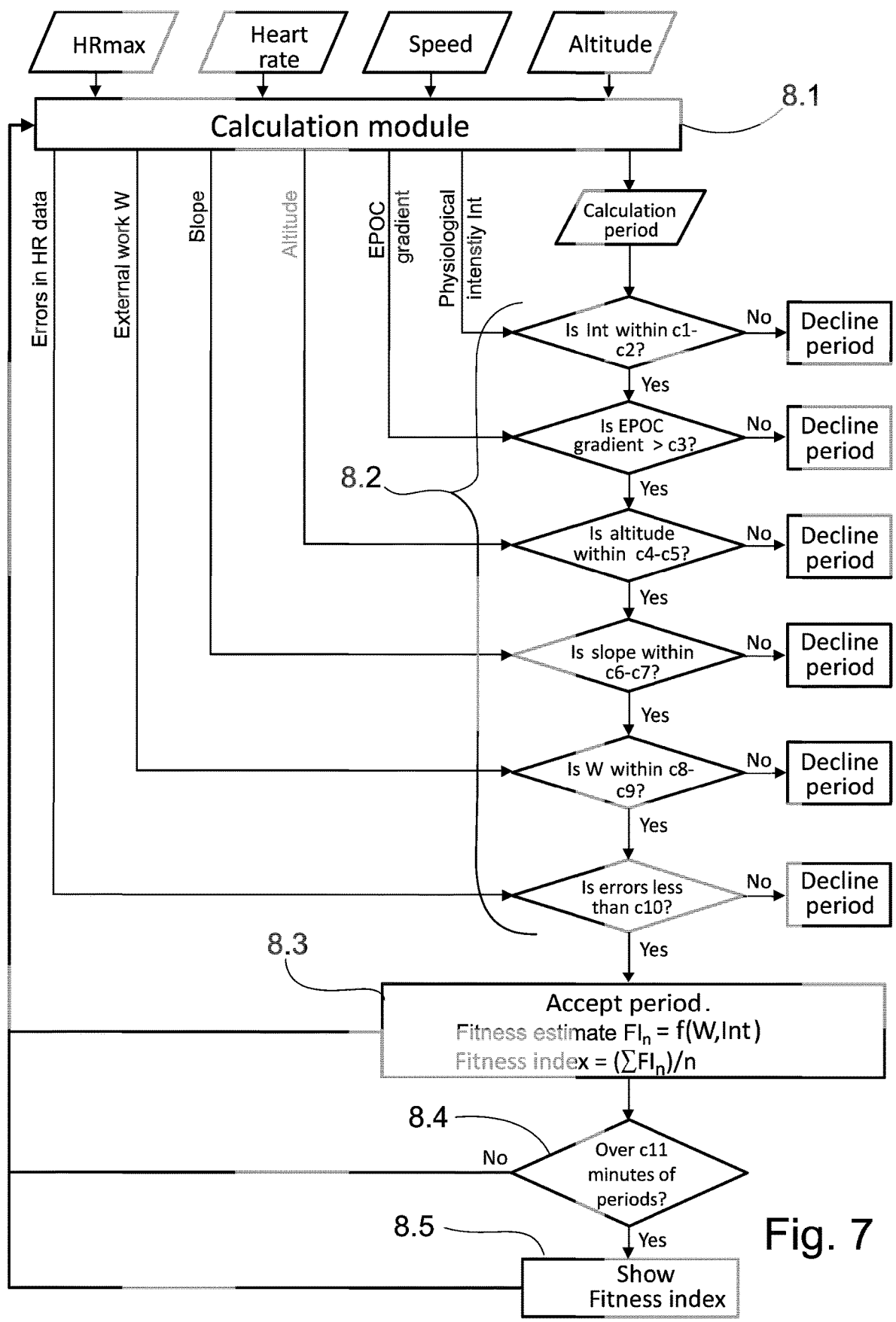
FIG. 7 shows a way to calculate a fitness index.

FIG. 7 shows the calculation of a fitness index, for example, during running or walking. The person's maximum heart rate (HRmax), heart rate (heartbeats per minute), speed (e.g., m(k)/h), and altitude (metres) are entered in the computation register. Each period being examined must be reliable, in order to create a fitness index. Reliability can be examined, for example, by setting reliability for known influencing factors, in this example external work (W), angle altitude, EPOC gradient, physiological intensity, limit values ($c1, c2 \ldots c9$), within the framework of which the variables must remain during the period being examined, for the period to be accepted. If the period is determined to be reliable, a fitness index is calculated for it, with the aid of external work (W) and physiological intensity (Int). So that the real fitness index can be shown reliably, the total time or number of the accepted periods must exceed the time/value ($c10$) regarded as reliable.

Figure 8:
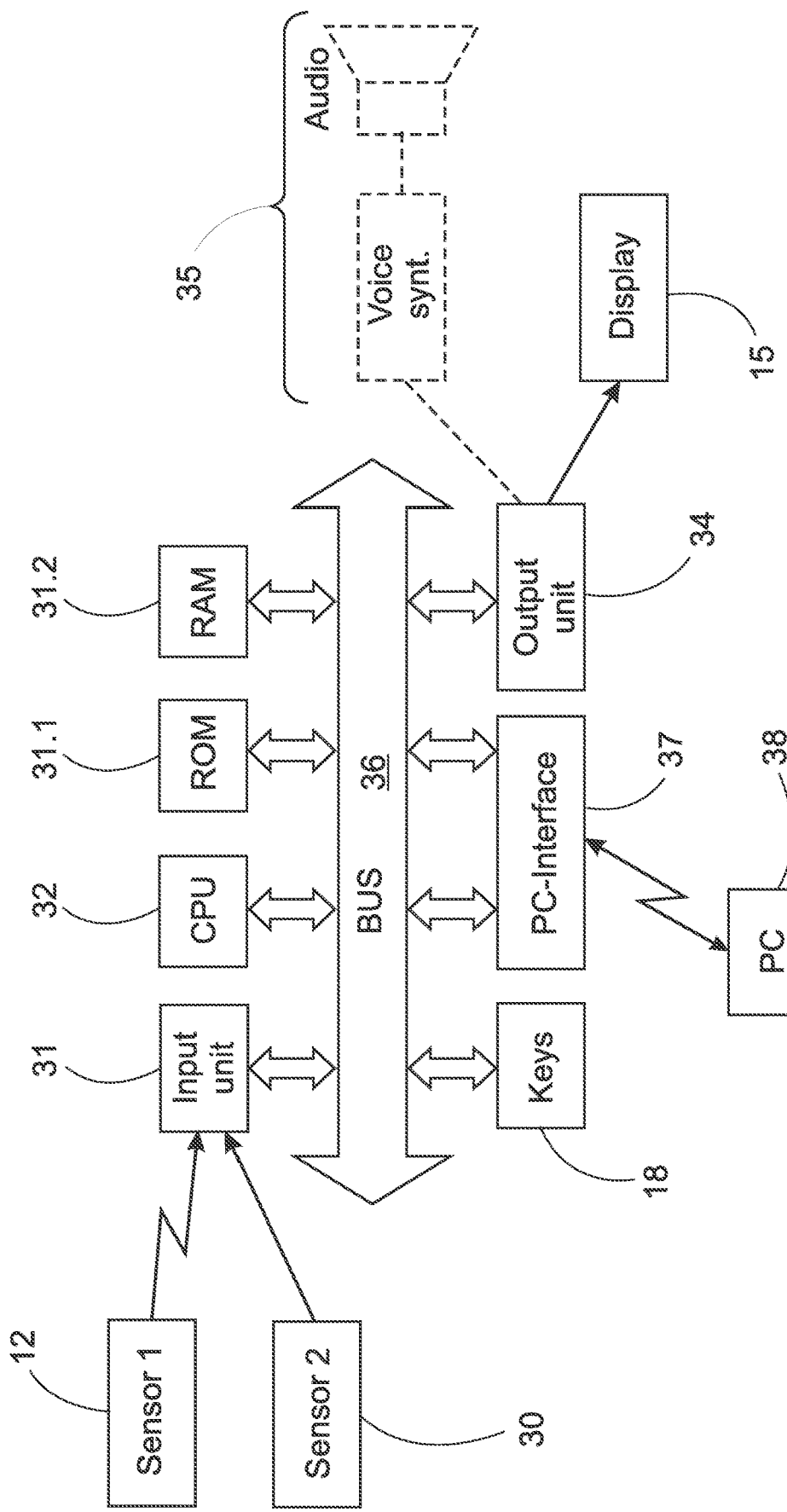
FIG. 8 shows a block diagram of the system in a wristop device.

According to FIG. 8, in a typical application (e.g., wristop device) the implementation comprises an assembly built around a central processing unit (CPU) 32. A bus 36 transmits data between the central unit 32 and the other units. The input unit 31, ROM memory 31.1, RAM memory 31.2, keypad 18, PC connection 37, and output unit 34 are connected to the bus.

The heartrate sensor 12 and some sensor 30 registering external output are connected to the input unit 31, which handles the sensor's data traffic to the bus 36. Optionally, the PC is connected to a PC connection 37. The output device, for example a display 15, is connected to the output unit 34. In some embodiments, voice feedback is created with the aid of a voice synthesizer and a loudspeaker 35, instead or, or in addition to the feedback on the display. The sensor 30 measuring external work can, in fact, comprise a group of sensors, which are used together to define the external work done by the user.

All of the default values of the optional parameters are preferably stored in a ROM memory, or more specifically, e.g. in an EEPROM (Electrically Erasable Programmable Read-Only Memory) memory.

For example, the user's "external" data:
sex man, age 35 years, weight 75 kg, height 180 cm.
User's more demanding data:
fitness level (VO$_2$max) 40 ml/kg/min; Activity class 4.

In a web service, the default values of the parameters are preferably recorded in self-service software.

In these embodiments, it would be as such also possible to use some other method than that described above as a fitness test. However, the fitness test according to the invention provides several advantages in terms of automatic updating. It can be completely integrated in many standard-model wristop devices and demands substantially fewer calculation stages than the method according to the WO publication.

The invention can be applied, for example, in the following applications: wristop device, mobile/cellphone application or device, fitness device, computer software, or web service.

REFERENCES

Jackson, A.; Blair, S.; Mahar, M.; Weir, L.; Ross, R.; and Stuteville, J.; 1990: "Prediction of functional aerobic capacity without exercise testing". Medicine and Science in Sports and Exercise, 22(6): 863-870.

McArdle, W. D.; Katch, F. I.; and Katch, V. L.; 2000: "Exercise Physiology: energy, nutrition, and human performance", 5$^{th}$ ed. Baltimore, Williams and Wilkins.

The invention claimed is:

1. A method for determining the cardiorespiratory fitness level of a person, with the aid of freely performed exercise, comprising:

measuring by a first sensor, a physiological intensity of the person during the exercise session in periods and storing each measured physiological intensity in computation registers; measuring by a second sensor an external work output of the exercise session simultaneously relative to the measured physiological intensity on each period, and storing each measured external output in the computation registers;

determining by an assembly built around a central processing unit (CPU), at each period whether the physiological intensity has stabilized relative to the external work output on the measured period in order to accept the period using a following criteria:
the physiological intensity is stabilized relative to the external work output, and
the external work output is within a selected range;

defining by the assembly built around the central processing unit, a fitness level estimate for each accepted period using a modeled function by entering into it the relative heart rate and external work of the accepted segment and the stored physiological intensity and the stored measured external output in the computation registers, and storing each defined fitness level estimate as accepted data points;

counting the total duration/number of accepted periods; and if said total duration/number exceeds a selected time/value, computing by the assembly built around the central processing unit, a fitness index with the aid of the fitness level estimates in the accepted data as an average with the aid of the defined fitness level estimates, if the total duration/number of accepted periods exceeds a selected time/value.

2. The method according to claim 1, wherein a variable depicting the change in cumulative homeostasis, is calcu-

TABLE 2

| NAME | STAGE | TRAINING | | | | | | | DURATION OF STAGE (WEEK) | NUMBER OF SESSIONS/ WEEK | HOURS/ WEEK | ORIGINAL ACTIVITY CLASS | MINIMUM ACTIVITY CLASS |
|---|---|---|---|---|---|---|---|---|---|---|---|---|---|
| | | 1 | 2 | 3 | 4 | 5 | 6 | 7 | | | | | |
| Start | 1 | TE | 2 | | 3 | | | 2 | | 4 | 3 | 1.33 | 0-2 | 0 |
| | | Durat. | 30 | | 25 | | | 25 | | | | | | |
| Improving 1 | 2 | TE | 2 | | 3 | | | 2 | | 4 | 3 | 1.5 | 3 | 3 |
| | | Durat. | 30 | | 25 | | | 35 | | | | | | |
| Improving 2 | 3 | TE | 1 | 2 | 3 | | 2 | | | 4 | 4 | 3 | 4 | 4 |
| | | Durat. | 45 | 60 | 30 | | 45 | | | | | | | |
| Improving 3 | 4 | TE | 2 | 3 | 1 | | 3 | | | 4 | 4 | 3.75 | 5-7 | 5 |
| | | Durat. | 75 | 60 | 45 | | 45 | | | | | | | |
| Improving 4 | 5 | TE | 3 | 2 | | 2 | 3 | | 1 | 4 | 5 | 5.25 | 7.5 --> | 6 |
| | | Durat. | 35 | 85 | | 75 | 60 | | 60 | | | | | |
| "Maintain" HARD | 6 | TE | 4 | 2 | | 4 | 3 | | 3 | 1 | 5 | 4.83 | | 7 |
| | | Durat. | 60 | 45 | | 50 | 75 | | 60 | | | | | |
| "Maintain" EASY | 7 | TE | | 2 | | 1 | 2 | | 1 | 1 | 4 | 4.75 | | |
| | | Durat. | | 75 | | 80 | 70 | | 60 | | | | | |
| "Maintain" MODERATE | 8 | TE | 3 | 2 | 1 | 2 | | 3 | 1 | 1 | 6 | 6.5 | | |
| | | Durat. | 50 | 90 | 45 | 90 | | 70 | 45 | | | | | | lated continuously, and the value of the variable depicting homeostasis should be increasing, in order for the period to be accepted.

3. The method according to claim 1, wherein each value of the fitness level (FIn) is obtained from the modelled function by entering into it the relative heart rate and external work of the accepted segment.

4. The method according to claim 1, wherein a sum of energy consumption kcal is calculated by steps of:
correcting heartbeat interval data by automatic error correction, RR data being always between two consecutive heartbeats;
calculating respiratory frequency information from the heartbeat interval data;
calculating heart rate per minute from the heartbeat interval data;
converting the heart rate to % of the person's maximum heart rate, using the person's maximum heart rate, where the maximum heart rate is defined on the basis of the person's age, if the person does not know it directly;
calculating the on/off kinematic information (loading stage) on the basis of the respiratory frequency and % HRmax;
calculating % VO2max or METmax intensity as percentages relative to the person's maximum, where the RQ (respiratory quotient) value is calculated giving a ratio of fats and carbohydrates as energy sources;
calculating the RQ relates to a known way to calculate energy consumption on the basis of oxygen consumption, wherein oxygen consumption (litre/minute) is multiplied by five, giving the energy consumption in calories;
converting the relative intensity % VO2max to absolute oxygen consumption by multiplying it by the person's VO2max (maximum oxygen consumption), wherein
if the person does not know their VO2max value, calculating it using Jackson et al.'s 1990 equation, on the basis of the person's background data, or obtaining VO2max value on the basis of an automatic fitness test;
calculating a calorific equivalent is calculated telling on the basis of the RQ value how much energy is produced per litre of oxygen consumed;
calculating the momentary energy consumption kcal/min; and
calculating the sum of energy consumption kcal is calculated from plurality of momentary.

5. A system for determining the level of the cardiorespiratory fitness level of a person, with the aid of freely performed exercise, comprising:
an interface device containing input devices for entering optional user-specific starting parameters before training, and a feedback device for providing feedback;
a memory register for recording the values of the said parameters and the calculation variables;
first means for measuring and recording a variable proportional to physiological intensity in periods and for storing each measured physiological intensity in the memory register;
second means for registering and recording external work output simultaneously relative to the measured physiological intensity on each period, and storing each measured external output in the memory register;
third means for determining whether the physiological intensity has stabilized relative to the external work output on the measured period in order to accept the period;
fourth means for determining the representativeness of the values of the intensity and external work recorded from simultaneous periods, in order to determine an accepted period in terms of fitness level, where the representative periods are those periods that have the following properties:
the physiological intensity must have stabilized relative to the external work output,
the external work output must be within a preselected range, and
the physiological intensity must be greater than a set criterion (x % HRmax); and
fifth means for defining a fitness-level estimate for each accepted period, using a modelled function and the stored physiological intensity and stored measured external output in the memory register, and for storing each defined fitness level estimate as accepted data and to define a fitness index in the memory register as an average of the defined fitness level estimates 2.

6. The system according to claim 5, wherein the system includes means for calculating continuously a variable, depicting the change in cumulative homeostasis, in which case the fourth means are arranged to accept periods, in which the variable depicting the change in homeostasis is increasing.

7. The system according to claim 5, further comprising:
means to determine the user's activity class, with the aid of initial data and a defined fitness index, using preselected criteria.

8. The system according to claim 7, wherein the said preselected criterion for determining the activity class comprises a 3-dimensional table with the following variables: sex, age, and fitness index.

9. The system according to claim 7, wherein the system includes means to determine the user's activity class, with the aid of initial data and a defined fitness index, using preselected criteria.

10. The system according to claim 5, wherein the external work output is arranged to be determined on the basis of running speed and slope.

11. The system according to claim 5, wherein the system is arranged to perform updating of the fitness index after each training session.

12. The system according to claim 11, wherein the system is arranged to calculate the fitness index from two or more training sessions and to weight the fitness index of each training session according to how many accepted periods are found from the training session.

13. The system according to claim 5, wherein the system is arranged to calculate the energy consumption during training.

14. The system according to claim 5, wherein the system is arranged to calculate the training effect (TE) caused by the training.

15. The system according to claim 5, wherein the system is arranged to define a training program according to the calculated fitness index.

* * * * *